United States Patent [19]

Wood

[11] Patent Number: 4,852,580

[45] Date of Patent: Aug. 1, 1989

[54] CATHETER FOR MEASURING BIOIMPEDANCE

[75] Inventor: Roger Wood, Paramount, Calif.

[73] Assignee: Axiom Medical, Inc., Paramount, Calif.

[21] Appl. No.: 119,294

[22] Filed: Nov. 6, 1987

Related U.S. Application Data

[63] Continuation of Ser. No. 908,185, Sep. 17, 1986, abandoned.

[51] Int. Cl.[4] ............................................. A61B 5/02
[52] U.S. Cl. ................................... 128/693; 128/713; 128/734; 128/642
[58] Field of Search .............. 128/693, 691, 734, 741, 128/642, 786, 802, 783–784, 713

[56] References Cited

U.S. PATENT DOCUMENTS

| | | |
|---|---|---|
| Re. 30,101 | 9/1979 | Kubicek et al. |
| 3,871,359 | 3/1975 | Pacela |
| 3,882,851 | 5/1975 | Sigworth |
| 3,903,897 | 9/1975 | Woollons et al. ............... 128/642 X |
| 3,915,174 | 10/1975 | Preston ............................ 128/786 X |
| 3,994,284 | 11/1976 | Voelker |
| 3,996,925 | 12/1976 | Djordjevich |
| 4,030,509 | 6/1977 | Heilman et al. ................. 128/784 X |
| 4,314,095 | 2/1982 | Moore et al. .................... 128/642 X |
| 4,380,237 | 4/1983 | Newbower ........................ 128/693 |
| 4,444,195 | 4/1984 | Gold ................................ 128/786 X |
| 4,450,527 | 5/1984 | Sramek |
| 4,476,872 | 10/1984 | Perlin .............................. 128/642 |
| 4,498,481 | 2/1985 | Lemke .............................. 128/734 |
| 4,548,211 | 10/1985 | Harks .............................. 128/693 X |
| 4,587,975 | 5/1986 | Salo et al. ....................... 128/693 |
| 4,674,518 | 6/1987 | Salo ................................ 128/734 X |
| 4,676,253 | 6/1987 | Newman et al. .................. 128/693 |
| 4,706,688 | 11/1987 | Don-Michael et al. ......... 128/642 X |

FOREIGN PATENT DOCUMENTS 8603391 6/1986 United Kingdom ................ 128/734

OTHER PUBLICATIONS

Baker et al.; "Desophageal Multipurpose Monitoring Probe"; *Anaesthesia*, vol. 38, 1983, pp. 892–897.

*Primary Examiner*—Kyle L. Howell
*Assistant Examiner*—Angela D. Sykes
*Attorney, Agent, or Firm*—Fulwider, Patton, Rieber, Lee & Utecht

[57] ABSTRACT

This invention is directed to an improved impedance sensing system to measure blood flow and particularly cardiac output which comprise an elongated flexible catheter having two spaced apart sensing electrodes disposed on the surface thereof formed from a conductive fabric such as metallic screen. Preferably, a pair of current transmitting electrodes are also positioned on the catheter each being outside of the pair of sensing electrodes.

11 Claims, 1 Drawing Sheet

U.S. Patent   Aug. 1, 1989   4,852,580
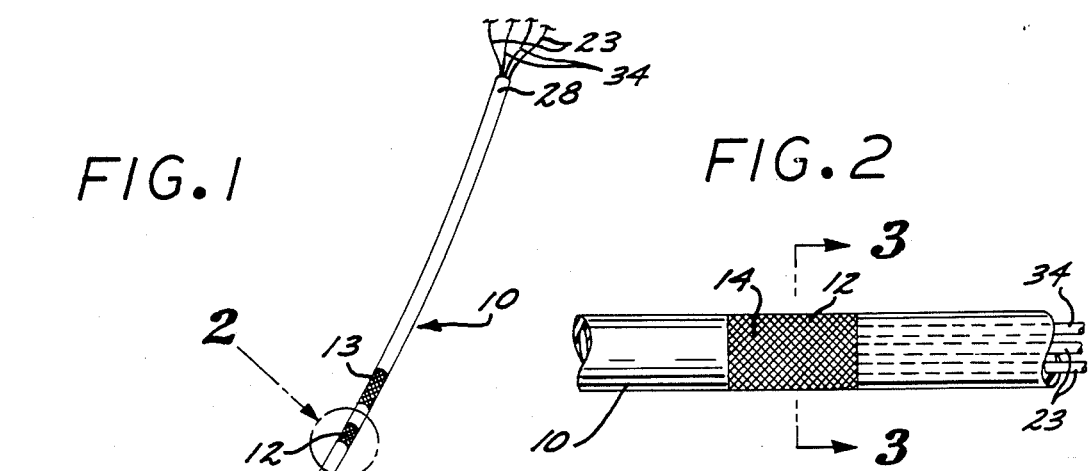
FIG. 1
FIG. 2
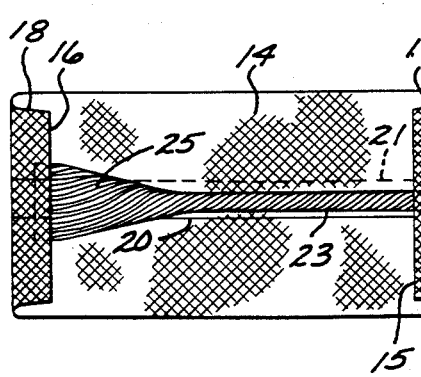
FIG. 3
FIG. 4
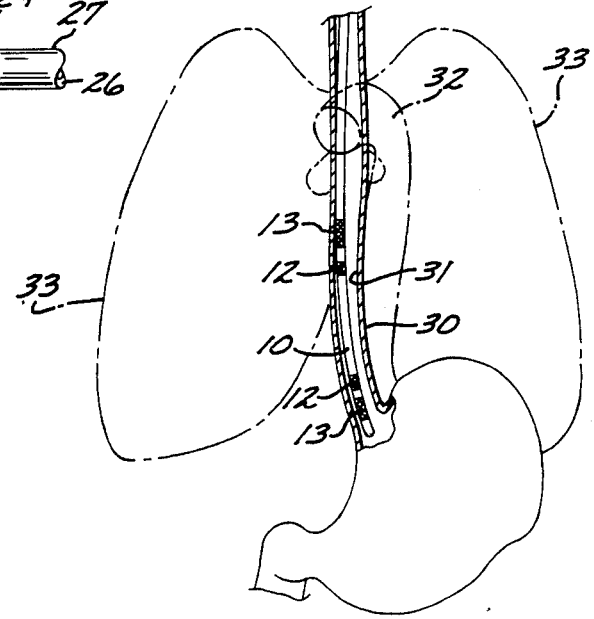
FIG. 5

CATHETER FOR MEASURING BIOIMPEDANCE

This application is a continuation of application Ser. No. 908,185, filed Sept. 17, 1986, now abandoned.

BACKGROUND OF THE INVENTION

This invention generally relates to the determination of blood flow through a body segment by detecting changes in the impedance of the segment which result from the blood flow. The invention has the particular utility in the determination of cardiac output.

Prior methods of determining blood flow from body impedance changes usually include subjecting a body segment to a high frequency electrical current and measuring the resultant voltage variations which represent impedance variations caused by the blood flow through the body segment. The impedance method of blood flow detection, often called impedance plethysmography, is based on the fact that blood has a much higher conductivity than the muscle, bone, and other tissue in the body segment. When the body segment is subjected to a high frequency electrical current, the changes in impedance are inversely proportional to the amount of blood therein. Prior systems for detecting impedance changes caused by blood flow or blood volume variations are generally described in the following list of references which is considered exemplary not exhaustive.

| PATENT NO. | PATENTEE |
| --- | --- |
| Re30,101 | Kubicek et al. |
| U.S. Pat. No. 3,882,851 | Sigworth |
| U.S. Pat. No. 3,871,359 | Pacela |
| U.S. Pat. No. 3,994,284 | Voelker |
| U.S. Pat. No. 3,996,925 | Djordjevich |
| U.S. Pat. No. 4,450,527 | Sramek |

For further information, reference is also made to the article by Kubicek et al. "The Minnesota Impedance Cardiography - Theory and Applications," Biochem Eng. 9:410, 1974 which describes some of the basic work done on impedance detection to determine cardiac output.

As is evident from the above references, high frequency electrical current is usually applied to the body segment by means of spaced apart transmitting electrodes which are positioned on the surface of the body segment in question. The impedance of the body segment is determined by spaced apart sensing electrodes which are disposed on the surface of the body segment between the two current transmitting electrodes. Both spot and wrap-around electrodes have been described in the prior art. The sensing electrodes usually measure voltage which is directly proportional to the impedance.

As indicated in U.S. Pat. No. 4,450,527 (Sramek), one of the major problems in determining cardiac output by detecting changes in thoracic impedance is to minimize the effects of pulmonary expansion and contraction on thoracic impedance because the pulmonary effects greatly exceed the effects of cardiac output on thoracic impedance. The prior art methods of electronically and/or mathetmatically manipulating the sensed impedance signal to reduce the pulmonary effects has improved cardiac output determinations. However, this method has not met with widespread acceptance due in part to the fact that the sensing system may not have the sensitivity to accurately determine cardiac output. Moreover, the methods described are not very suitable for measuring cardiac output during thoracic surgery.

Thus, a substantial need remains for accurately determining cardiac output, particularly during thoracic surgery. The present invention responds to this need by providing a sensing system having greater sensitivity for detecting impedance and one which may be used during thoracic surgery.

SUMMARY OF THE INVENTION

The present invention is directed to an improved system for measuring the bioimpedance changes resulting from variations in blood volume on a body segment and particularly for accurately determining cardiac output.

The improved system in accordance with the invention comprises an elongated, flexible catheter having spaced apart electrodes on the outer surface thereof for sensing signals representing impedance which results from the application of high frequency electrical current to the bodily segment. The signal sensed by the two sensing electrodes is a voltage signal which is proportional to the bioimpedance of the body segment between the two sensing electrodes, which in turn is related to the blood volume within the body segment.

The catheter of the invention is designed primarily to be inserted into the esophagus where the two sensing electrodes are positioned therein adjacent the descending thoracic aorta. In this position, the impedance changes sensed are very responsive to blood flow through the thoracic aorta and much less effected by pulmonary activity than prior sensing systems.

The sensing electrodes which are formed from a conductive fabric, are positioned on the outer surface of the catheter in a manner which does not interfere or otherwise impede the oral or nasal insertion of the catheter into the esophagus. Preferably, the electrodes are cylindrically shaped, with the outer diameter of the cylinder being equal to or slightly smaller than the outer diameter of the catheter. A particularly suitable conductive material is stainless steel mesh, having a mesh size from about 50 to 1000 (Tyler), preferably from about 300 to 500 (Tyler).

The conductive fabric greatly increases the sensitivity of the electrodes and provides a significant improvement in impedance measurement. To improve the electrical contact between the electrodes and the inner lining of the esophagus, the the electrode may be coated with an electrically conductive gel such as is used when taking an electrocardiogram.

For esophageal use, the sensing electrodes should be spaced apart by about 6 to 12 inches (approximately 15 to 30 cm).

In a preferred embodiment of the catheter, a pair of electrical current transmitting electrodes are spaced along the length of the catheter outwardly of the sensing electrodes. The transmitting electrodes generally are of the same structure and composition as the sensing electrodes but generally are slightly longer than the sensing electrodes to provide a greater surface area.

The impedance signal picked up by the pair of sensing electrodes associated with the catheter may be used to calculate the blood flow in any suitable manner such as those methods described in the prior art references previously listed. The method described in U.S. Pat. No. 4,450,527 (Sramek) is presently preferred and the teachings of this patent are hereby incorporated in their entirety by reference thereto.

These and other advantages of the invention will become more apparent from the following detailed description of the invention when taken in conjunction with the accompanying exemplary drawings.

BRIEF DESCRIPTION OF THE DRAWINGS

FIG. 1 illustrates an catheter which embodies features of the invention;

FIG. 2 is an enlarged view of the encircled electrode shown in FIG. 1;

FIG. 3 is a cross-sectional view taken along the lines 3—3 of FIG. 2;

FIG. 4 is a cross-sectional view taken along the lines of 4—4 in FIG. 3 with the catheter portions removed; and FIG. 5 is a front view partially in section illustrating the positioning of the catheter within an esophagus.

DETAILED DESCRIPTION OF THE INVENTION

Reference is made to FIG. 1 which represents a catheter 10 which embodies features of the invention. As shown, the distal end 11 of catheter 10 is provided with sensing electrodes 12 which are preferably disposed between the two current transmitting electrodes 13. FIGS. 2-4 show the details of a sensing electrode 12. The transmitting electrodes 13 are preferably of the same construction as sensing electrodes 12 except for being a little longer in order to provide more surface area for contact with adjacent tissue. The electrode 12 comprises a cylindrical shaped conductive fabric 14 formed of a material such as metal or conductive plastic material which is compatible with the tissues it contacts and which is otherwise suitable for the environment in which it is to be used. The presently preferred fabric is stainless steel wire screen with a mesh size from about 50 to 1000 (Tyler) and optimally from about 300-500 (Tyler).

The electrode 12 may be made from a rectangular piece of the desired conductive fabric. The opposing ends 15 and 16 of the screen 14 are folded over to form hems 17 and 18, as shown in FIG. 4. The screen 14 is formed into the cylindrical shape of electrode 12 with the opposing sides 20 and 21 being overlapped and joined by suitable means, e.g., resistance welding, as shown in FIG. 3. A stranded conductor 23 passes through a opening 24 in the proximal end 15 of the screen 14 and is held in electrical contact with the screen 14 on the interior thereof by means of the hems 17 and 18 of the screen 14 which are formed by folding over the ends 15 and 16 of the screen 14. The stranded conductor 23 is preferably flared at the end 25 thereof to provide better electrical contact with the screen 14. The portion of the electrical conductor 23 outside of the electrode 12 is provided with insulation 26 and preferably a shielding cover 27. The insulated portion of conductors 23 from each electrode 12 and 13 preferably pass through the wall of the catheter 10 into the interior thereof and extend beyond the proximal end 28 of the catheter 10, as shown in FIG. 1.

The sensing electrodes 12 are spaced from one another along the length of catheter 10 by about 6 to 12 inches (approximately 15 to 30 cm) with the shorter distances being for children and the longer distances for adults. The transmitting electrodes 13 are disposed outside of sensing electrodes 12, at a distance therefrom of about 0.5 to 2 inches (approximately 1.25 to 5.1 cm). The length of the electrodes may range from about 0.1 to about 1 inch (0.25 to 2.5 cm). The transmitting electrodes 13 are preferably about 25 to 200 percent longer than the sensing electrode 12. The outer diameters of the electrodes 12 and 13 are essentially the same or slightly smaller than the outer diameter of the catheter 10 which preferably vary from about .05 to about 0.5 inch (approximately 1.6 to 16 mm) which is equivalent to catheter sizes of 12 to 40 French.

The placement of the catheter 10 within the esophagus 31 is shown in FIG. 5. As indicated, the sensing and transmitting electrodes 12 and 13, respectively, are in very close proximity to the descending thoracic aorta 32, which results in an impedance measurement which is much less effected by the activity of the lungs 33 so that substantially more accurate blood flow determinations can be made. If desired, the catheter may be provided with an inflatable collar or bladder, which when inflated secures the position of the catheter 10 within the esophagus.

When using metallic screen, there should not be any loose wire ends or electrode rough surfaces or edges which might damage the lining 30 of the esophagus 31 or the oral or nasal pasasgeways (not shown) during the insertion and withdrawal thereof. Preferably, the conductive fabric 14 of the electrodes 12 and 13 is covered with a conductive cream or jelly to improve electrical contact between the electrodes and the lining 30 of the esophagus 31 shown in FIG. 5. The jelly or cream also acts as a lubricant to facilitate the oral or nasal insertion of the catheter 10 into the esophagus 31.

The metallic screen 14 may be plated with a more conductive metal, e.g., silver, to improve the electrical contacts and thereby reduce contact resistance.

The electrical conductors 24 from the sensing electrodes 12 and electrical conductors 34 from the transmitting electrodes 13 pass through the interior of the catheter 10 and exit the proximal end 28 thereof. The conductors 34 from the transmitting electrodes 13 are connected to a constant high frequency electrical current source (not shown) as described in U.S. Pat. No. 4,450,527 and conductors 24 from the sensor electrodes 12 are connected to the electronic system, as described in U.S. Pat. No. 4,450,527 to determine the impedance of the body segment from the sensed signal.

Although the impedance sensing system of the invention has been described herein in terms of mounting onto an esophageal catheter, it should be recognized that other types of catheters can be used. Moreover, other modifications can be made to the present invention without departing from the scope thereof.

What is claimed is:

1. An elongated, flexible catheter adapted to be inserted into a patient's esophagus for measuring the bioimpedance of a thoracic ssection thereof in order to determine the patient's cardiac output, the catheter having on the outer surface of a distal portion thereof a pair of axially spaced apart, cylindrically shaped sensing electrodes formed of conductive fabric, and a pair of axially spaced apart, cylindrically shaped transmitting electrodes, one of the transmitting electrodes disposed proximally to the pair of sensing electrodes and one of the transmitting electrodes disposed distally to the pair of sensing electrodes with axial spacing between each transmitting electrode and the adjacent sensing electrode being at least as great as the outer diameter of the catheter, the pair of transmitting electrodes being adapted to contact tissue on the inner wall of the patient's esophagus in order to apply high frequency electrical current to the thoracic section and the pair of sensing electrodes being adapted to contact tissue on the inner wall of the patient's esophagus in order to detect electrical signals therefrom which result from the application of high frequecy electrical current to the body section by the transmitting electrodes, the electrical signals sensed by the sensing electrodes being related to the bioimpedance of the thoracic section.

2. The catheter of claim 1 wherein the sensing electrodes are formed into cylindrical shapes from conductive fabric and encircle the outer periphery of the catheter.

3. The catheter of claim 2 wherein the conductive fabric is a metallic screen having a mesh size of about 50 to 1000 (Tyler).

4. The catheter of claim 3 wherein the metallic screen has a mesh size of about 300 to 500 (Tyler).

5. The catheter of claim 4 wherein the metallic screen is stainless steel.

6. The catheter of claim 5 wherein the transmitting electrodes are from about 25 to 200 percent longer than the sensing electrodes.

7. The catheter of claim 1 wherein the transmitting electrodes are formed from conductive fabric into cylindrical shapes and are mounted on the outer surface of the catheter.

8. The catheter of claim 7 wherein electrical conductors are disposed within the interior of the catheter, pass through the wall of the catheter, and are electrically connected to the electrodes disposed on the outer surface thereof.

9. The catheter of claim 1 wherein the catheter is formed from flexible material selected from the group consisting of natural rubbers and elastomers.

10. The catheter of claim 1 wherein the sensing electrodes are spaced apart along the length of the catheter by a distance of about 6 to 12 inches.

11. The catheter of claim 1 wherein the diameter of the catheter ranges from about 0.05 to about 0.05 inch.

* * * * *